United States Patent
Daugherty et al.

(12)

(10) Patent No.: US 6,271,347 B1
(45) Date of Patent: *Aug. 7, 2001

(54) EOSINOPHIL EOTAXIN RECEPTOR

(75) Inventors: Bruce L. Daugherty, South Orange; Julie A. Demartino, Cranford; Salvatore J. Siciliano, East Brunswick; Martin S. Springer, Westfield, all of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/847,296

(22) Filed: Apr. 24, 1997

Related U.S. Application Data

(60) Provisional application No. 60/016,158, filed on Apr. 26, 1996, and provisional application No. 60/017,113, filed on Apr. 26, 1996.

(51) Int. Cl.[7] .......................... C07K 14/715; C12N 5/10; C12N 15/12; C12N 15/64
(52) U.S. Cl. ..................... 530/350; 435/69.1; 435/70.1; 435/71.1; 435/71.2; 435/252.3; 435/254.11; 435/320.1; 435/325; 435/471
(58) Field of Search .......................... 530/350; 435/69.1, 435/70.1, 71.1, 71.2, 172.3, 325, 252.3, 320.1, 254.11, 671

(56) References Cited

U.S. PATENT DOCUMENTS 5,215,915 * 6/1995 Tiberi et al. .................... 435/252.3

FOREIGN PATENT DOCUMENTS

WO 96/22371  7/1996 (WO) .

OTHER PUBLICATIONS

Neote et al. Cell, vol. 72, pp. 415–425, 1993.*
Combadiere et al. J. of Biol. Chem. vol. 270, No. 27, pp. 16491–16494, Jul. 1995.*
Baggiolini, *J. Clin. Invest.*, 97 (3), 587 (Feb. 1996) "Editorial —Exotaxin: A VIC (Very Important Chemokine) of Allergic Inflammation?".
Combadiere, et al., *J. Biol. Chem.*, 270 (27) 16491–16494 (1995) "Cloning and Functional Expression of a Human Eosinophil CC Chemokine Receptor".
Combadiere, et al., *J. Biol. Chem.*, 270 (27) 16491–19494 (1995) "Additions and Corrections".
Daugherty, et al., *J. Exp. Med.*, 183, 2349–2354 (May 1996) "Cloning, Expression and Characterization of the Human Eosinophil Eotaxin Receptor".
Kita, et al., *J. Exp. Med.*, 183, 2421–2426 (Jun. 1996) "Chemokines Active on Eosinophils: Potential Roles in Allergic Inflammation".
Kitaura, et al., *J. Biol. Chem.*, 271 (13) 7725–7730 (Mar. 29, 1996) "Molecular Cloning of Human Eotaxin . . . and Identification of a Specific Eosinophil Eotaxin Receptor, CC Chemokine Receptor 3".
Ponath, et al., *J. Exp. Med.*, 183 2437–2448 (Jun. 1996) "Molecular Cloning and Characterization of a Human Eotaxin Receptor Expressed Selectively on Eosinophils".
Ponath, et al., *J. Clin. Invest.*, 97 (3) 604–612 (Feb. 1996) "Cloning of the Human Eosinophil Chemoattractant Eotaxin".

* cited by examiner

*Primary Examiner*—Prema Mertz
(74) *Attorney, Agent, or Firm*—J. Eric Thies; David L. Rose

(57) ABSTRACT

The eosinophil eotaxin receptor has been isolated, cloned and sequenced. This receptor is a human β-chemokine receptor and has been designated "CC CKR3". The eosinophil eotaxin receptor may be used to screen and identify compounds that bind to the eosinophil eotaxin receptor. Such compounds would be useful in the treatment and prevention of atopic conditions including allergic rhinitis, dermatitis, conjunctivitis, and particularly bronchial asthma.

4 Claims, No Drawings

EOSINOPHIL EOTAXIN RECEPTOR

CROSS REFERENCE TO RELATED APPLICATIONS

This application claims priorty under 35 U.S.C. §119(e) from provisional application No. 60/017,113, filed Apr. 26, 1996 and from provisional application No. 60/016,158, filed Apr. 26, 1996.

FIELD OF THE INVENTION

This invention relates to an eosinophil eotaxin receptor ("CC CKR3"), in particular, the human eosinophil eotaxin receptor and nucleic acids encoding this receptor. This invention further relates to assays which may be used to screen and identify compounds that bind to the eosinophil eotaxin receptor. Such compounds would be useful in the treatment and prevention of atopic conditions including allergic rhinitis, dermatitis, conjunctivitis, and particularly bronchial asthma.

BACKGROUND OF THE INVENTION

Eosinophils play prominant roles in a variety of atopic conditions including allergic rhinitis, dermatitis, conjunctivitis, and particularly bronchial asthma (for a reviews see e.g. Gleich, G. J., et al., *Eosinophils*. J. I. Gallin, I. M. Goldstein, R. Snyderman, Eds., Inflammation: Basic Principles and Clinical Correlates (Raven Press, Ltd., New York, 1992) and Seminario, M. C., et al. (1994) *Current Opinion in Immunology* 6, 860–864). A pivotal event in the process is the accumulation of eosinophils at the involved sites. While a number of the classical chemoattractants, including C5a, LTB4, and PAF, are known to attract eosinophils (Gleich, G. J., et al., *Eosinophils*. J. I. Gallin, et al. Eds., Inflammation: Basic Principles and Clinical Correlates (Raven Press, Ltd., New York, 1992)), these mediators are promiscuous, acting on a variety of leukocytes including neutrophils, and are unlikely to be responsible for the selective accumulation of eosinophils. In contrast, the chemokines a family of 8–10 kDa proteins are more restricted in the leukocyte subtypes they target and are potential candidates for the recruitment of eosinophils in atopic diseases and asthma (Baggiolini, M., Dewald, B. and Moser, B. (1994) *Advances in Immunology* 55, 97–179). Although there is a mounting body of evidence that eosinophils are recruited to sites of allergic inflammation by a number of β-chemokines, particularly eotaxin and RANTES, the receptor which mediates these actions has not been identified.

The chemokines contain four conserved cysteines, and are divided into two sub-families based on the arrangement of the first cysteine pair (Baggiolini, M., Dewald, B. and Moser, B. (1994) *Advances in Immunology* 55, 97–179). In the α-chemokine family, which includes IL-8, MGSA, NAP-2 and IP-10, these two cysteines are separated by a single amino acid, while in the β-chemokine family, which includes RANTES ("regulated on activation T expressed and secreted"), MCP-1 ("monocyte chemotactic protein"), MCP-2, MCP-3, MIP-1α ("macrophage inflammatory protein"), MIP-1β and eotaxin, these two cysteines are adjacent. There is a functional correlate to this structural division. The α-chemokines act primarily on neutrophils, and the β-chemokines on monocytes, lymphocytes, basophils and eosinophils (Baggiolini, M., Dewald, B. and Moser, B. (1994) *Advances in Immunology* 55, 97–179). In particular, RANTES, MCP-2, MCP-3, and MIP-1α have been shown to activate eosinophils in vitro (Dahinden, C. A., et al. (1994) *Journal of Experimental Medicine* 179, 751–756; Ebisawa, M., et al. (1994) *Journal of Immunology* 153, 2153–2160; Weber, M., et al. (1995) *Journal of Immunology* 154, 4166–4172), and RANTES to selectively attract eosinophils in vivo (Meurer, R., et al. (1993) *Journal of Experimental Medicine* 178, 1913–1921; Beck, L., et al. (1995) *FASEB Journal* 9, A804). Similarly, eotaxin, a new member of the β-chemokine family, first described in guinea pigs (Griffiths-Johnson, D. A., et al. (1993) *Bichemical and Biophysical Research Communications* 197, 1167–1172; Jose, P. J., et al. (1994) *Journal of Experimental Medicine* 179, 881–887) and mice (Rothenberg, et al. (1995) *Proceedings of the National Academy of Sciences* 92, 8960– 8964) is also a potent attractant and activator of eosinophils both in vitro and in vivo. Moreover, eotaxin is generated during antigenic challenge in the guinea pig model of allergic airway inflammation (Jose, et al. (1994) *J. Exp. Med.,* 179, 881–887; Rothenberg, et al. (1995) *J. Exp. Med.,* 181, 1211–1216. The cloning of guinea pig eotaxin has been disclosed (PCT Patent Publication No. WO 95/07985; Mar. 23, 1995). The cloning of the human eosinophil chemoattractant eotaxin has recently been reported (Ponath, et al., *J. Clin. Invest.* (1996) 97(3) 604–612) and eotaxin has been suggested to be a very important agent in the mechanism of allergic inflammation (Baggiolini, et al., *J. Clin. Invest.* (1996) 97(3) 587).

Eosinophils are attracted by a number of β-chemokines, the most potent of which are eotaxin (Griffiths-Johnson, D. A., et al. (1993) *Bichemical and Biophysical Research Communications* 197, 1167–1172; Jose, P. J., et al. (1994) *Journal of Experimental Medicine* 179, 881–887; Rothenberg, et al. (1995) *Proceedings of the National Academy of Sciences* 92, 8960–8964) and RANTES (Dahinden, C. A., et al. (1994) *Journal of Experimental Medicine* 179, 751–756; Ebisawa, M., et al. (1994) *Journal of Immunology* 153, 2153–2160; Weber, M., et al. (1995) *Journal of Immunology* 154, 4166–4172; Meurer, R., et al. (1993) *Journal of Experimental Medicine* 178, 1913–1921; Beck, L., et al. (1995) *FASEB Journal* 9, A804). Although several human β-chemokine receptors have been characterized in detail, none have the appropriate selectivity to account for the observed responses.

While elucidation of the actions of β-chemokines on eosinophils has contributed greatly to the understanding of eosinophil biology, information regarding the cell surface receptors which mediate these effects remain sparse. Furthermore, there are no reports describing binding studies of any of the β-chemokines to primary eosinophils. The known β-chemokine receptors are members of the G protein-coupled receptor superfarnily. Two of these receptors, CC CKR1 (12, 13) and CC CKR2 (MCP-1R) (Charo, I. F., et al. (1994) *Proceecing of the National Academy of Sciences* 91, 2752–2756; Myers, S. J., et al. (1995) *Journal of Biological Chemistry* 270, 5786– 5792; Franci, C., et al. (1995) *Journal of Immunology* 154, 6511–6517) found on monocytes, have been extensively studied and their selectivity for the different chemokines defined. However, neither of these receptors has the necessary ligand selectivity or the appropriate expression patterns required to mediate the effects of the β-chemokines on eosinophils. For example, CC CKR1 binds RANTES with high affinity, but binds eotaxin poorly, and while the effects of eotaxin on CC CKR2 have not been studied this receptor has no avidity for RANTES (Myers, S. J., et al. (1995) *Journal of Biological Chemistry* 270, 5786–5792).

A review of the role of chemokines in allergic inflammation is provided by Kita, H., et al., *J. Exp. Med.* 183, 2421–2426 (June 1996). In particular, this review discusses the role which the receptor CKR-3 plays in the process of allergic inflammation. The cloning, expression and characterization of the human eosinophil eotaxin receptor has been reported by Daugherty, B. J., et al., *J. Exp. Med.* 183, 2349–2354 (May 1996). This publication discloses the cloning and functional expression of the chemokine receptor CC CKR3, as well as its characterization.

The cloning and expression of a human eosinophil receptor was allegedly achieved by Combadiere, C., et al., *J. Biological Chem.* 270 (27), 16491–16494 (Jul. 14, 1995). However, in a subsequent retraction (*J. Biological Chem.* 270, 30235 (1995)) they confirmed that the receptor which was actually cloned and expressed was not CC CKR3, but was another CC chemokine receptor CC CKR5. This receptor was subsequently characterized by Kitaura, M., et al., *J. Biological Chem.* 271 (13), 7725–7730 (Mar. 29, 1996).

A human eotaxin receptor has been reported by Ponath, P. D., et al. *J. Exp. Med.* 183, 2437–2448 (June 1996) and Gerard, C. J., et al., PCT Publication No. WO 96/22371 (Jul. 25, 1996). However, the sequence disclosed in this publication possesses an error in the assignment of threonine rather than serine at position #276 of the receptor. In addition, functionality of the receptor was not fully demonstrated.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, *N. Engl. J. Med.*, 335(20), 1528–1530 (Nov. 14 1996). The principal cofactor for entry mediated by the envelope glycoproteins of primary macrophage-trophic strains of HIV-1 is CCR5, a receptor for the β-chemokines RANTES, MIP-1α and MIP-1β (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that β-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1α and MIP-1β (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro apper to be unusually resistant to HIV-1 infection and are not immunocompromised by the presence of this genetic variant (*Nature*, 382, 722–725 (1996)). Absence of CCR-5 appears to confer protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). The determination that chemokine receptors are critical co-receptors for the entry of HIV into cells was pronounced a "1996 Breakthrough of the Year" by Science Magazine (*Science*, 274, 1987–1991 (Dec. 20, 1996)).

The use of orally-active agents which modulate the action of the eosinophil eotaxin receptor would be a significant advance in the treatment and prevention of atopic conditions including allergic rhinitis, dermatitis, conjunctivitis, and particularly bronchial asthma. Further, agents which could block the eosinophil eotaxin receptor in humans who possess normal chemokine receptors should prevent infection in healthy individuals and slow or halt viral progression in infected patients.

It would also be desirable to know the molecular structure of the eosinophil eotaxin receptor in order to analyze this new receptor family and understand its normal physiological role. This could lead to a better understanding of the in vivo processes which occur upon ligand-receptor binding. Further, it would be desirable to use cloned-eosinophil eotaxin receptor as essential components of an assay system which can identify new agents for the treatment and prevention of atopic conditions.

SUMMARY OF THE INVENTION

The present invention relates to a novel receptor which is the eosinophil eotaxin receptor. This receptor is a human β-chemokine receptor and has been designated "CC CKR3". One aspect of the present invention is directed to the human eosinophil eotaxin receptor, free from receptor-associated proteins. A further aspect of this invention is the human eosinophil eotaxin receptor which is isolated or purified.

Another aspect of this invention are eosinophil eotaxin receptors which are encoded by substantially the same nucleic acid sequences, but which have undergone changes in splicing or other RNA processing-derived modifications or mutagenesis induced changes, so that the expressed protein has a homologous, but different amino acid sequence from the native forms. These variant forms may have different and/or additional functions in human and animal physiology or in vitro in cell based assays.

The present invention further provides the eosinophil eotaxin receptor, CC CKR3, which is a β-chemokine receptor and which was cloned from primary eosinophils, and expressed in AML14.3D10 cells. This receptor binds the potent eosinophil attractants, eotaxin, RANTES and MCP-3 with high affinity. In addition, eotaxin and RANTES, and to a lessor extent MCP-3, induce $Ca^{2+}$-fluxes in cells expressing CC CKR3. Correlation with the binding properties of primary eosinophils provide conclusive evidence that CC CKR3 is the primary endogenous receptor which mediates the effects of β-chemokines on eosinophils.

The present invention further relates to assays which employ a novel receptor which is the eosinophil eotaxin receptor. This receptor is a human β-chemokine receptor and has been designated "CC CKR3". One aspect of the present invention is directed to assays employing the the human eosinophil eotaxin receptor, free from receptor-associated proteins. A further aspect of this invention is directed to assays which employ the human eosinophil eotaxin receptor which is isolated or purified. In addition, the present invention provides assays in which the eosinophil eotaxin receptor is expressed in an AML14.3D10 cell line.

DETAILED DESCRIPTION OF THE INVENTION

The present invention is directed to an eosinophil eotaxin receptor "CC CKR3" which is a G protein-coupled receptor and has been cloned from human eosinophils and which when stably expressed in AML14.3D10 cells binds eotaxin, RANTES and MCP-3 with high affinity. Competition binding studies against $^{125}$I-human eotaxin gives Kd values of 0.1, 2.7, and 3.1 nM, respectively for the three β-chemokines. CC CKR3 also binds MCP-1 with lower affinity, but does not bind MIP-1α or MIP-1β. Eotaxin, RANTES, and to a lessor extent MCP-3, but not the other chemokines activate CC CKR3 as determined by the ability to stimulate a $Ca^{2+}$-flux in clones expressing the receptor. Competition binding studies on primary eosinophils give binding affinities for the different chemokines which are indistinguishable from those measured with CC CKR3. Since CC CKR3 is prominently expressed in eosinophils it is concluded that CC CKR3 is the eosinophil eotaxin receptor. Eosinophils also express a much lower level of a second chemokine receptor, CC CKR1, which appears to be responsible for the effects of MIP-1α.

The eosinophil eotaxin receptor is a protein containing various functional domains, including one or more domains which anchor the receptor in the cell membrane, and at least one ligand binding domain. As with many receptor proteins, it is possible to modify many of the amino acids, particularly those which are not found in the ligand binding domain, and still retain at least a percentage of the biological activity of the original receptor. In accordance with this invention, it is suggested that certain portions of the eosinophil eotaxin receptor are not essential for its activation by β-chemokines. Thus this invention specifically includes modified functionally equivalent eosinophil eotaxin receptors which have deleted, truncated, or mutated portions. This invention also specifically includes modified functionally equivalent eosinophil eotaxin receptors which contain modified and/or deletions in other domains, which are not accompanied by a loss of functional activity.

Additionally, it is possible to modify other functional domains such as those that interact with second messenger effector systems, by altering binding specificity and/or selectivity. Such functionally equivalent mutant receptors are also within the scope of this invention.

A further aspect of this invention are nucleic acids which encode an eosinophil eotaxin receptor or a functional equivalent from human or other species. These nucleic acids may be free from associated nucleic acids, or they may be isolated or purified. For most cloning purposes, cDNA is a preferred nucleic acid, but this invention specifically includes other forms of DNA as well as RNAs which encode an eosinophil eotaxin receptor or a functional equivalent.

Yet another aspect of this invention relates to vectors which comprise nucleic acids encoding an eosinophil eotaxin receptor or a functional equivalent. These vectors may be comprised of DNA or RNA; for most cloning purposes DNA vectors are preferred. Typical vectors include plasmids, modified viruses, bacteriophage and cosmids, yeast artificial chromosomes and other forms of episomal or integrated DNA that can encode an eosinophil eotaxin receptor. It is well within the skill of the ordinary artisan to determine an appropriate vector for a particular gene transfer or other use.

A further aspect of this invention are host cells which are transformed with a gene which encodes an eosinophil eotaxin receptor or a functional equivalent. The host cell may or may not naturally express an eosinophil eotaxin receptor on the cell membrane. Preferably, once transformed, the host cells are able to express the eosinophil eotaxin receptor or a functional equivalent on the cell membrane. Depending on the host cell, it may be desirable to adapt the DNA so that particular codons are used in order to optimize expression. Such adaptations are known in the art, and these nucleic acids are also included within the scope of this invention.

The receptors of this invention were cloned from RNA isolated from eosinophils. Degenerate PCR was used with primers designed from both CCCKR1 and CCCKR2, and clones screened by expression in the AML14.3D10 cell line. The cloning was made difficult by several factors. First, prior to this invention there was very little information available about the biochemical characteristics and intracellular signalling/effector pathways used by these receptors making screening procedures uncertain. Second, this receptor could not be expressed and/or functionally coupled in the cell lines normally used for cloning receptors such, as COS, CHO, HEK293. After repeated failures using standard lines, an obscure eosinophilic-like cell line, AML14.3D10, was tried and found to suitable for expression of the receptors described in this invention.

The present invention further relates to assays which employ a novel receptor which is the eosinophil eotaxin receptor. This receptor is a human β-chemokine receptor and has been designated "CC CKR3". One aspect of the present invention is directed to assays employing the the human eosinophil eotaxin receptor, free from receptor-associated proteins. A further aspect of this invention is directed to assays which employ the human eosinophil eotaxin receptor which is isolated or purified. In addition, the present invention provides assays in which the eosinophil eotaxin receptor is expressed in an AML14.3D10 cell line.

A particular embodiment of this invention is directed to an assay to determine the presence of a compound which binds to the eosinophil eotaxin receptor. Thus, this invention also comprises a method to determine the presence of a compound which binds to an eosinophil eotaxin receptor comprising:

(a) introducing a nucleic acid which encodes an eosinophil eotaxin receptor into a cell under conditions so that eosinophil eotaxin receptor is expressed;

(b) introducing a detector molecule or a nucleic acid encoding a detector molecule into the cell, wherein the detector molecule is directly or indirectly responsive to a eosinophil eotaxin-ligand binding event;

(c) contacting the cell with a compound suspected of binding to the eosinophil eotaxin receptor; and (d) determining whether the compound binds to the eosinophil eotaxin receptor by monitoring the detector molecule.

In a preferred embodiment of the present invention, the eosinophil eotaxin receptor is expressed in AML14.3D10 cells.

In another preferred embodiment of the present invention, the binding of the compound suspected of binding to the eosinophil eotaxin receptor is compared to the binding or the influence of eotaxin, RANTES and MCP-3.

A further embodiment of this invention is directed to an assay to determine the presence of a compound which antagonizes the binding of a known ligand to the eosinophil eotaxin receptor. Thus, this invention further comprises a method to determine the presence of a compound which antagonizes the eosinophil eotaxin receptor comprising:

(a) introducing a nucleic acid which encodes the eosinophil eotaxin receptor into a cell under conditions so that eosinophil eotaxin receptor is expressed;

(b) introducing a detector molecule or a nucleic acid encoding a detector molecule into the cell, wherein the detector molecule is directly or indirectly responsive to an eosinophil eotaxin-ligand antagonism event;

(c) contacting the cell with a compound suspected of antagonizing the eosinophil eotaxin receptor;

(d) contacting the cell with a compound which is a known ligand of the eosinophil eotaxin receptor; and (e) determining whether the compound antagonizes the action of the known ligand to the eosinophil eotaxin receptor by monitoring the detector molecule.

In a preferred embodiment of the present invention, the eosinophil eotaxin receptor is expressed in AML14.3D10 cells.

In another preferred embodiment of the present invention, the known ligand of the eosinophil eotaxin receptor is eotaxin, RANTES and MCP-3.

One aspect of this invention is the development of a sensitive, robust, reliable and high-throughput screening assay which may be used to detect ligands which bind to the eosinophil eotaxin receptor, in particular, antagonists of the action of chemokines on eosinophils.

In particular, a typical protocol of such an assay is as follows. Assay buffer (50 mM Hepes, pH 7.2 w/0.5% BSA, 5 mM $MgCl_2$, 1 mM $CaCl_2$, 100 uM PMSF and 10 ug/ml phosphoramidon, leupeptin, aprotinin and chymostatin), test compound (or equivalent volume of solvent), 20 pM $^{125}$I-human eotaxin (2000 Ci/mmol), 25 ng unlabeled human eotaxin (non-specific binding wells only), and AML14.3D10 cells expressing eotaxin receptor cells, or eosinophils, are added sequentially in 96-well, round-bottom, polystyrene plates to a final volume of 250 uL. Assay plates are then mixed and incubated for 60 minutes at 31° C. After incubation, assay plates are harvested onto Packard 96-well GF/C Unifilter plates treated with 0.33% polyethylenimine (PEI) using Packard Filtermate 196 cell harvester. Wells and filters are washed with 200 uL 50 mM Hepes, pH 7.2 with 0.5M NaCl and 0.02% NaN3. After filtration, GF/C plates are dried and sealed. 25 uL Packard Microscint-O scintillant are then added to each well and counted for 2 minutes on Packard Topcount (liquid $^{125}$I setting).

Ligands detected using assays described herein may be used in the treatment and prevention of conditions which would be benefited by the modification of the activity of the eosinophil eotaxin receptor, such as in the treatment and prevention of atopic conditions including allergic rhinitis, dermatitis, conjunctivitis, and particularly bronchial asthma.

A further aspect of this invention is directed to novel ligands which are identified using the subject assays.

The eosinophil eotaxin receptor and fragments are immunogenic. Thus, another aspect of this invention is antibodies and antibody fragments which can bind to eosinophil eotaxin receptor or an eosinophil eotaxin receptor fragment. These antibodies may be monoclonal antibodies and produced using either hybridoma technology or recombinant methods. They may be used as part of assay systems or to deduce the function of an eosinophil eotaxin receptor present in a cell.

A further aspect of this invention are antisense oligonucleotides nucleotides which can bind to eosinophil eotaxin receptor nucleotides and modulate receptor function or expression.

A further aspect of this invention is a method of increasing the amount of eosinophil eotaxin receptor in a cell comprising, introducing into the cell a nucleic acid encoding an eosinophil eotaxin receptor, and allowing expression of the eosinophil eotaxin receptor.

As used throughout the specification and claims, the following definitions shall apply:

Ligand—any molecule which binds to an eosinophil eotaxin receptor of this invention. These ligands can have either agonist, partial agonist, partial antagonist or antagonist activity.

Free from receptor-associated proteins—the receptor protein is not in a mixture or solution with other membrane receptor proteins.

Free from associated nucleic acids—the nucleic acid is not covalently linked to DNA which it is naturally covalently linked in the organism's chromosome.

Isolated receptor—the protein is not in a mixture or solution with any other proteins.

Isolated nucleic acid—the nucleic acid is not in a mixture or solution with any other nucleic acid.

Functional equivalent—a receptor which does not have the exact same amino acid sequence of a naturally occurring eosinophil eotaxin receptor, due to alternative splicing, deletions, mutations, or additions, but retains at least 1%, preferably 10%, and more preferably 25% of the biological activity of the naturally occurring receptor. Such derivatives will have a significant homology with the natural eosinophil eotaxin receptor and can be detected by reduced stringency hybridization with a DNA sequence obtained from an eosinophil eotaxin receptor. The nucleic acid encoding a functional equivalent has at least about 50% homology at the nucleotide level to a naturally occurring receptor nucleic acid.

Purified receptor—the receptor is at least about 95% pure.
Purified nucleic acid—the nucleic acid is at least about 95% pure.

Single-letter abbreviations for amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

Orphan Cloning of an Eosinophil Chemokine Receptor

RT/PCR conducted using oligonucleotide primers developed from the amino acid residues clustered within transmembrane helicies II (TMII) and VII (TMVII) of the β-chemokine receptors, CC CKR1 (Neote, K., et al. (1993) *Cell* 72, 415–425) and MCP-lR (Charo, I. F., et al. (1994) *Proceecing of the National Academy of Sciences* 91, 2752–2756) on total RNA isolated from eosinophils yielded DNA fragments of ~700 bases, a size consistent with that expected for a G protein coupled receptor. Analysis of several TMII to TMVII clones provided a novel sequence which was 76% homologous with human CC CKR1 at the nucleic acid level. Completion of the cloning of the 3' and 5' ends gave a sequence for a protein of 355 residues in length, 63% identical to CC CKR1, and 51% identical to CC CKR2B, its closest homologues.

The amino acid sequence of the human eosinophil eotaxin receptor CC CKR3 is depicted below (SEQ ID NO: 1):

```
Met Thr Thr Ser Leu Asp Thr Val Glu Thr Phe Gly Thr Thr Ser
Tyr Tyr Asp Asp Val Gly Leu Leu Cys Glu Lys Ala Asp Thr Arg
Ala Leu Met Ala Gln Phe Val Pro Pro Leu Tyr Ser Leu Val Phe
Thr Val Gly Leu Leu Gly Asn Val Val Val Met Ile Leu Ile
Lys Tyr Arg Arg Leu Arg Ile Met Thr Asn Ile Tyr Leu Leu Asn
Leu Ala Ile Ser Asp Leu Leu Phe Leu Val Thr Leu Pro Phe Trp
Ile His Tyr Val Arg Gly His Asn Trp Val Phe Gly His Gly Met
Cys Lys Leu Leu Ser Gly Phe Tyr His Thr Gly Leu Tyr Ser Glu
Ile Phe Phe Ile Ile Leu Leu Thr Ile Asp Arg Tyr Leu Ala Ile
Val His Ala Val Phe Ala Leu Arg Ala Arg Thr Val Thr Phe Gly
Val Ile Thr Ser Ile Val Thr Trp Gly Leu Ala Val Leu Ala Ala
Leu Pro Glu Phe Ile Phe Tyr Glu Thr Glu Glu Leu Phe Glu Glu
Thr Leu Cys Ser Ala Leu Tyr Pro Glu Asp Thr Val Tyr Ser Trp
Arg His Phe His Thr Leu Arg Met Thr Ile Phe Cys Leu Val Leu
Pro Leu Leu Val Met Ala Ile Cys Tyr Thr Gly Ile Ile Lys Thr
Leu Leu Arg Cys Pro Ser Lys Lys Lys Tyr Lys Ala Ile Arg Leu
Ile Phe Val Ile Met Ala Val Phe Phe Ile Phe Trp Thr Pro Tyr
Asn Val Ala Ile Leu Leu Ser Ser Tyr Gln Ser Ile Leu Phe Gly
Asn Asp Cys Glu Arg Ser Lys His Leu Asp Leu Val Met Leu Val
Thr Glu Val Ile Ala Tyr Ser His Cys Cys Met Asn Pro Val Ile
Tyr Ala Phe Val Gly Glu Arg Phe Arg Lys Tyr Leu Arg His Phe
Phe His Arg His Leu Leu Met His Leu Gly Arg Tyr Ile Pro Phe
Leu Pro Ser Glu Lys Leu Glu Arg Thr Ser Ser Val Ser Pro Ser
Thr Ala Glu Pro Glu Leu Ser Ile Val Phe
```

The sequence for the cDNA encoding the human eosinophil eotaxin receptor CC CKR3 beginning with nucleotide 3587 and ending with nucleotide 4651 is depicted below (SEQ ID NO:2):

```
                                        ATGA CAACCTCACT
3601 AGATACAGTT GAGACCTTTG GTACCACATC CTACTATGAT GACGTGGGCC
3651 TGCTCTGTGA AAAAGCTGAT ACCAGAGCAC TGATGGCCCA GTTTGTGCCC
3701 CCGCTGTACT CCCTGGTGTT CACTGTGGGC CTCTTGGGCA ATGTGGTGGT
3751 GGTGATGATC CTCATAAAAT ACAGGAGGCT CCGAATTATG ACCAACATCT
3801 ACCTGCTCAA CCTGGCCATT TCGGACCTGC TCTTCCTCGT CACCCTTCCA
3851 TTCTGGATCC ACTATGTCAG GGGGCATAAC TGGGTTTTTG GCCATGGCAT
3901 GTGTAAGCTC CTCTCAGGGT TTTATCACAC AGGCTTGTAC AGCGAGATCT
3951 TTTTCATAAT CCTGCTGACA ATCGACAGGT ACCTGGCCAT TGTCCATGCT
4001 GTGTTTGCCC TTCGAGCCCG GACTGTCACT TTTGGTGTCA TCACCAGCAT
4051 CGTCACCTGG GGCCTGGCAG TGCTAGCAGC TCTTCCTGAA TTTATCTTCT
4101 ATGAGACTGA AGAGTTGTTT GAAGAGACTC TTTGCAGTGC TCTTTACCCA
4151 GAGGATACAG TATATAGCTG GAGGCATTTC CACACTCTGA GAATGACCAT
```

-continued

```
4201 CTTCTGTCTC GTTCTCCCTC TGCTCGTTAT GGCCATCTGC TACACAGGAA

4251 TCATCAAAAC GCTGCTGAGG TGCCCCAGTA AAAAAAAGTA CAAGGCCATC

4301 CGGCTCATTT TTGTCATCAT GGCGGTGTTT TTCATTTTCT GGACACCCTA

4351 CAATGTGGCT ATCCTTCTCT CTTCCTATCA ATCCATCTTA TTTGGAAATG

4401 ACTGTGAGCG GAGCAAGCAT CTGGACCTGG TCATGCTGGT GACAGAGGTG

4451 ATCGCCTACT CCCACTGCTG CATGAACCCG GTGATCTACG CCTTTGTTGG

4501 AGAGAGGTTC CGGAAGTACC TGCGCCACTT CTTCCACAGG CACTTGCTCA

4551 TGCACCTGGG CAGATACATC CCATTCCTTC CTAGTGAGAA GCTGGAAAGA

4601 ACCAGCTCTG TCTCTCCATC CACAGCAGAG CCGGAACTCT CTATTGTGTT

4651 T
``` or a degenerate variation thereof.

The 5' genomic DNA flanking sequence encoding the human eosinophil eotaxin receptor further comprises the region beginning with nucleotide 1 and ending with nucleotide 3586 as depicted below (SEQ ID NO:3):

```
   1 GGATCCCTAC CTTCCCCATC AGAGCTAGGG GGCATGGAGC GCTCTCTGCT

51 AAGATGGGGA CCCCCAAGGA ATGTCTCCCT GTGGGGCACT TCCTTACCAG

101 ATGGGATGGC CAGTGCGGTT AAGTTGGTGG TCAGGCAGAA AAAAAAGATC

151 TAGTTTGTAC TCTTGAGAGT TCCTCGGTTT GTTCATGGCA TGGGCAGGGA

201 GTCAAGGAGC AGCAGCCTTG CCTCAGTGCC TACCAGTGCA GGAAAAGGTG

251 CATAGCCTGG GCCAGGGCCA GGGCCCTGGT GGAGGCGTAG TGGTAACAGA

301 GAGGGCTCTC CATTCCAGCC CAAGGAAGAC TAAGAATGAA TACCTCATGA

351 GTATATTAGC TACAAACCAC CACAGCAGGT TCCAGAAAAA GGCTCAGCGT

401 TGGAACCAGG TCACCCCCAC TCAGCAGACA CCAGTCATAT AAATCAAGGA

451 CCAACAGGAG ACAGGAACAC CCCCTTCCCA CTCTGCCCCA TGTCTCAAGT

501 TGTAGTGGCC CTTCCTCCAG ATCTCTGCCA CCATCTTAGA AAGGAACACT

551 GAAAGAAGAA ACTGAAATTA TAAGCTGACA GCATAAAGAG GATGAGTAAA

601 ACCTAAAATC ATTGTTCACA TGAATGAATC AAGAGAAGTT TAAACCACTT

651 TGGACTAAAA TGTGTGAATC CTTTTTCCTG CTATCCAGCA GATGAGAAGC

701 TGGTAACAGA GACCACAATA GTTTGGAGAC TAAAGAATCA TTGCACATTT

751 CACTGCTGAG TTGTATTGTG AGTAATTTTA GTTGACCTCA CTTTGTAAAT

801 CTTGCACACG GGGCAATCCA ATATCTGCAC AAGAGATATG TTAACCAGTG

851 GTAAATGCTG CATGAGGAGA TTGGGTGATT TTTACTTTCG TTTTTGTGCT

901 CTTCTTTCTT ATTGTTCTTA CTTATTTACG ATTACCCTAT CGTTTTCCCA

951 AAATGTAAAA GGCCATTTTG AAAGCCTAAT TCAAACCTCT TCACTATTTT

1001 GTATCTAAGT ATTCACCTTG ATTGAGACTG GGTAGACAGG TGAAAACCAT

1051 ATCAGGTTTT TAATTTTTTA ATTTTTAATT ATTTATTTAT TTATTTATTT

1101 TTTGAGATGG AGTCTGGCTG TCGCCCAGGC TGGAGTGCAG CGGCGTGATC

1151 ACAGTTCACT GCAGCCTCAA CCTTCTAGGC TCAAGGGATT CTCCCACCTC

1201 AGCCCCCCAA GTAGTTGGGA CCACACGTAT GCGCCACCAT GCCTGGCTAA
```

-continued

```
1251 TTTCTTATTT TTTTGTAGAG ATAGGATCTC ACTATATTGT CCAGGCTGGT
1301 CTTGAATTCC TGGGCTCAGG TGAGCCTCCC ACCTGGGCCT CCCAAAGTAC
1351 TGGGATTACA GGCATGAGCC AAGGTCCCCT GCCCATATGA GATTTTCTGT
1401 CTCTGATCCC ATGCAGCTAG TAATCAAGGA CTTGGCTGCT GACTCTGGAG
1451 GACCTGCATG CTTTCTTGAG CTGTGAACTT CAGTGCTAAA AGCTCATAGG
1501 CAGCCCTGAA ACCCAAACCA AAAGGTTCTA TGGTTTATCA TCCTGATCAT
1551 GTTGATTTTA TAGAAATAAC ACATGAATTA AAGACACTAC CCTCAAACTG
1601 AGCAAAACTT AAGTAATTTT TTTAAAGTTT GACCTGTTTT TAAATCACTC
1651 TTGGAGAAAA AGGAAAATAA ATACAAATAA TTAACGGTGA ATACAGGCTA
1701 CTATACCTTT GTTCTCCAGA ATTAGCAGTT CTGTTCTTTT CTTGCTTTAG
1751 ATGCTGAAGT GCAGAAGGAC ACTCTGTGAT TGTACGTGTG TAACTGACAA
1801 AATGTGTATT TTTTTTCTCA GCTGCTATGG ATTGGATTAT GCTATTATGA
1851 ATAAGAATGC TGATGGGAGC ACACACAAAC CATTTGTTCC TCAGTCCATT
1901 TTCCTCCTCA AAAGCCTGGA ATGTGCCATT GATCAGTGGG AGATGTACCT
1951 GGACAGACCC ATGAAAAGAG ATCAACAAGT TCCACCCAAG GGACCCTATT
2001 TTTCCTAATT TCATTTGAAA TGGCTTCTAA TTGTCCTTCT TTCATTCCTG
2051 CTTCCTACCA GTTTTACAGC TTTTTCTGGT TTCAAATGTG AACTCACATA
2101 CACTCTCATT TTTCCTCATC ACAACCCCAA GTGACCCAAT GGTCCTCACT
2151 TTCGATATAA GTAAAGGAGG CTCTGCATTA AGGGCTTGTC CAAGGCACGC
2201 AGCTGAGAGG CGCTAGGACT GGCTCCATTT CCATCTCTAT TCTCACTGAC
2251 TTTGACTACC CAGAACCCCA ACATGTGGGG CCTCAGTATT CGATCAATTA
2301 TTCTATTAAG AAGCAAAAAC AATTCCCCGC ATTGGCCCCA GTTATTAAGC
2351 ATTTCTCAGA TTTACCTTGA GAAATGCCCA TCGGCCTGTA TATTCACATC
2401 TTCACCCTTG TCCCTTCCTC CTAGAAAGGA GAAAGTCAGT TGGATGCCCT
2451 CTGAGGAACT AGTGCATGGC TTAACTGTCC TTCCATGACT CCTGCCTTAT
2501 CTGTTTTCTA TTTTCCTCCT TTTCCACCGA AGTCTATAAT CTCAAGAAAA
2551 GCAGGCACTG GCCTTAGGGC TCCTGGCCTA AGAAATATCA AGTCCAGTGA
2601 GAAATCCCAT TGACTGACCC CTCCTGCTTA CCCCTTTGTG ATGGAGAAGC
2651 TCCCAGGGGT TGCTTTTTG CATGTTACCA GGCCTAACTC AGCATCACCA
2701 GGGGCAAGAA AAGGAAAGTA ACCTAAACTA ATGCTGCTTA TAATTGTAAT
2751 TATTGTAATA GTTAATTACT GTGATTGTAC ATGTGTAACA GACAAAATGT
2801 GTATTTTTTT CACAGCTGCT GTGGATTGGA TTATGCCATT TGGAATAAGA
2851 ATGCTGTTAA GAGCACACAA GCCAGGTTCC TCAAGTCCGT AGCAAATTTT
2901 TCAAAAGTTA AATTTAAAAA TCACTACATT TGAATCTAGT GACAGGAGAA
2951 ATGGACATGG ATAGAGACTA AGATCTAGC CCAAATTTTA TATTTACTTG
3001 TTAGAGGATT TTGAACAAAT TACTAAATTT CTTCAAGGTT CAATTTCCCC
3051 ATTAACTATA ATGAATGTCT CATCATTATG GGGCCCTGGA GAAGCATAAT
3101 TACTTGTAAT TGTAATAATC ATTGTTATTA TTATTATACA TATTTTGCTT
3151 TTAAATGGAT AAGGATTTTT AAGGTATATG TAAACTGTAA AACATAAAAT
3201 GCAAAATGCC GTAAGAGACA GTAGTAATAA TAATGATTAT TATATTGTTA
```

-continued

```
3251 TCATTATCTA GCCTGTTTTT TCCTGTTGTG TATTTCTTCC TTTAAATGCT

3301 TACAGAAATC TGTATCCCCA TTCTTCACCA CCACCCCACA ACATTTCTGC

3351 TTCTTTTCCC ATGCCGGTCA TGCTAACTTT GAAAGCTTCA GCTCTTTCCT

3401 TCCTCAATCC TTCTCCTGGC ACCTCTGATA TGCCTTTTGA AATTCATGTT

3451 AAAGAATCCC TAGGCTGCTA TCACATGTGG CATCTTTGTT GAGTACATGA

3501 ATAAATCAAC TGGTGTGTTT TACGAAGGAT GATTATGCTT CATTGTGGGA

3551 TTGTATTTTT CTTCTTCTAT CACAGGGAGA AGTGAA
``` or a degenerate variation thereof.

The sequence for the cDNA encoding human eosinophil eotaxin receptor further comprises the terminator region beginning with nucleotide 4652 and ending with nucleotide 5099 as depicted below (SEQ ID NO:4):

```
4652 TAGGTCAGA TGCAGAAAAT TGCCTAAAGA GGAAGGACCA AGGAGATGAA

4701 GCAAACACAT TAAGCCTTCC ACACTCACCT CTAAAACAGT CCTTCAAACT

4751 TCCAGTGCAA CACTGAAGCT CTTGAAGACA CTGAAATATA CACACAGCAG

4801 TAGCAGTAGA TGCATGTACC CTAAGGTCAT TACCACAGGC CAGGGGCTGG

4851 GCAGCGTACT CATCATCAAC CCTAAAAAGC AGAGCTTTGC TTCTCTCTCT

4901 AAAATGAGTT ACCTACATTT TAATGCACCT GAATGTTAGA TAGTTACTAT

4951 ATGCCGCTAC AAAAAGGTAA AACTTTTTAT ATTTTATACA TTAACTTCAG

5001 CCAGCTATTG ATATAAATAA AACATTTTCA CACAATACAA TAAGTTAACT

5051 ATTTTATTTT CTAATGTGCC TAGTTCTTTC CCTGCTTAAT GAAAAGCTT
``` or a degenerate variation thereof.

As will be appreciated by one skilled in the art, there is a substantial amount of redundancy in the set of codons which translate specific amino acids. Accordingly, this invention also includes alternative base sequences wherein a codon (or codons) are replaced with another codon such that the amino acid sequence translated by the DNA sequences remains unchanged. For purposes of this specification, a sequence bearing one or more such replaced codons will be defined as a degenerate variation. Also included are mutations (exchanges of individual amino acids) which one skilled in the art would expect to have no effect on functionality, such as valine for leucine, arginine for lysine, and asparagine for glutamine.

The amino acid sequence of CC CKR3 shares some sequence homology with CC CKR1 (Neote, K., et al. (1993) *Cell* 72, 415–425), CC CKR2B (Charo, I. F., et al. (1994) *Proceecing of the National Academy of Sciences* 91, 2752–2756), CC CKR4 (Power, C. A., et al. (1995) *Journal of Biological Chemistry* 270, 19495–19500) and V28 (Raport, C. J., et al. (1995) *Gene* 163, 295–299). The sequence of this protein, designated CC CKR3, is comparable to that previously reported by Combadiere et al. (Combadiere, C., et al. (1995) *Journal of Biological Chemistry* 270, 16491–16494) except that it contains a lysine in place of asparagine at position 107. Genomic cloning provided confirmation of the subject sequence, including lysine at position 107. The sequence discrepancy, which results from a substitution of G to T at the third position of the codon for residue 107, could represent a genetic polymorphism. This is highly unlikely, however, because all α- and β-chemokine receptors analyzed to date contain lysine in that position including the recently described basophilic β-chemokine receptor (Power, C. A., et al. (1995) *Journal of Biological Chemistry* 270, 19495–19500), CC CKR1 (Neote, K., et al. (1993) *Cell* 72, 415–425), MCP-LR (Charo, I. F., et al. (1994) *Proceecing of the National Academy of Sciences* 91, 2752–2756), IL-8RA and IL-8RB (Holmes, W. E., et al. (1991) *Science* 253, 1278–1280; Murphy, P. M., et al. (1991) *Science* 253, 1280–1283), the three murine β-chemokine receptors (Post, T. W., et al. (1995) *Journal of Immunology* 155, 5299–5305; Gao, J. L., et al. (1995) *Journal of Biological Chemistry* 270, 17494–17501) as well as three human chemokine-like receptors (Loetscher, M., et al. (1994) *Journal of Biological Chemistry* 269, 232–237; Raport, C. J., et al. (1995) *Gene* 163, 295–299; Combadiere, C., et al. (1995) *DNA and Cell Biology* 14, 673–680; Federsppiel, B., et al. (1993) *Genomics* 16, 707–712). An unusual feature of CC CKR3 is the cluster of negatively charged amino acids (ETEELFEET) distal to TMIV in the second extracellular loop.

Expression of the Human CC CKR3 in AML14.3D10 Cells

Once a full length cDNA encoding CC CKR3 was isolated and cloned into the expression vector pBJ/NEO the resulting plasmid designated pBJ/NEO/CCCKR3, was transfected into the AML14.3D10 line.

The CC CKR3 transfected AML14.3D10 cell line has been placed on restricted deposit with American Type Culture Collection in Rockville, Md. as ATCC No. CRL-12079, on Apr. 5, 1996.

Stable clones were selected for neomycin resistance, and a number were chosen for further analysis. To demonstrate expression of receptor protein, a western blot was performed using antisera generated against a peptide derived from the predicted C-terminus of CC CKR3. Immunoreactive bands migrating at approximately 45–55 kd are present in primary eosinophils and the 3.16 clone, indicating that CC CKR3 is indeed expressed in these cells. There was no immunoreactive bands present in neutrophils indicating that the antisera was indeed identifying an eosinophil-specific protein. A nonspecific pattern of immuno-reactivity was detected in untransfected AML14.3D10 cells, and furthermore, this pattern was identical in clone 3.49 indicating that this neomycin-resistant clone is a non-expressor of CC CKR3. Of the 27 neomycin resistant clones studied, 19 failed to express CC CKR3. The other 8 did express the receptor as judged both by Western analysis, and by the ability of eotaxin and RANTES to induce $Ca^{2+}$-fluxes. The non-expressing clones were used as negative controls in subsequent experiments.

Binding to CC CKR3 on Intact AML14/CCCKR3.16 Cells

Because preliminary experiments with three different CC CKR3 expressing clones indicated that they bound $^{125}$I-eotaxin, competition studies using this labeled ligand were performed to characterize the binding properties of the receptor. As shown in Table 1, unlabeled human eotaxin competed with an Kd of 0.1 nM. Results with murine eotaxin were essentially identical. Scatchard analysis demonstrated that eotaxin binds with a single affinity and that the different clones expressed $2-4\times10^5$ receptors/cell. The ability to bind eotaxin is due to CC CKR3 since neither immunoreactive negative clones, such as 3.49, nor untransfected cells displayed any specific binding. Clearly, CC CKR3 is a high affinity receptor for eotaxin. Cross-competition studies with the two other β-chemokines known to be eosinophil chemoattractants, RANTES and MCP-3, demonstrated that they too have considerable affinity for CC CKR3, with Kd's of about 3 nM (See Table 1). In contrast, MCP-1 competed with much lower affinity (Kd=60 nM), and MIP-1α, and MIP-1β failed to compete at all (See Table 1). Similarly, the α-chemokine IL-8 did not inhibit eotaxin binding.

Competition studies were also carried out against 125I-MCP-3. Again, human and murine eotaxin competed strongly with Kd's of 0.2 and 0.3 nM (Table 1). RANTES and MCP-3 also demonstrated high affinity with Kd's of 0.5 and 0.7 nM, values about 4-fold lower than observed against eotaxin. As in the studies with eotaxin, MCP-1 competed weakly (Kd=16 nM), and MIP-1α, and MIP-1β failed to competete at all. Thus despite some small quantitative differences the overall ligand selectivity of the receptor is the same whether measured by competition against eotaxin or MCP-3, and the order of potency, eotaxin>MCP-3=RANTES>>MCP-1, is identical.

CC CKR3 is Functionally Coupled in AML14.3D10 Cells

In order to determine whether human CC CKR3 was functionally coupled when expressed in the AML14.3D10 line, intracellular $Ca^{2+}$ levels were measured in response to various β-chemokines. Both 100 nM eotaxin and RANTES induced $Ca^{2+}$-fluxes in cells expressing the receptor. Surprisingly, 1 μM of MCP-3 was required to induce a response, and that response was smaller than those observed for eotaxin or RANTES. No response at all was generated by addition of MIP-1α, MIP-1β, MCP-1 or IL-8 at concentrations as high as 1 μM. The responses to eotaxin, RANTES, and MCP-3 are due to the specific expression of CC CKR3 since none of these mediators induced fluxes in untransfected cells or in clone 3.49. While the preliminary functional characterization by Combadiere et. al. differs greatly from the present invention, they were not able to demonstrate any specific binding to cells putatively expressing the receptor, and such functional data have now been retracted (Combadiere, C., et al. (1995) *Journal of Biological Chemistry* 270, 30235).

Binding Properties of Primary Eosinophils

The selectivity of CC CKR3 for the various β-chemokines mirrors the effectiveness of these ligands as eosinophil chemoattractants suggesting that CC CKR3 is the primary mediator of chemokine induced eosinophil chemotaxis. To provide additional pharmacological evidence, binding studies were conducted on primary eosinophils. When measured by competition against $^{125}$I-eotaxin, unlabeled human eotaxin gave an Kd=0.1 nM, a value identical to that obtained on cloned CC CKR3 (see Table 1). Scatchard analysis showed a single binding affinity, and $4\times10^5$ sites/cell. The number of binding sites varied by less than 2-fold for the 3 donors used in the studies. The affinites for RANTES and MCP-3 were also identical to those measured on CC CKR3, and as with CC CKR3, neither MIP-1α, or MIP-1β, showed any ability to compete with radiolabeled eotaxin (see Table 1). Similarly, the Kd's obtained by competition against $^{125}$I-MCP-3 on eosinophils are effectively indistinguishable to those measured against cloned CC CKR3 (see Table 1). All of the observations and measurements, taken together with the Western blot showing expression of CC CKR3, verify that CC CKR3 is the eosinophil eotaxin receptor, and appears to be largely responsible for mediating the effects of most β-chemokines on eosinophils.

Stably expressed in the eosinophilic line AML14.3D10, CC CKR3 binds eotaxin, RANTES and MCP-3, with high affinity, with a rank order of potency of eotaxin>RANTES=MCP-3. MCP-1 binds with much lower affinity, while MIP-1α and MIP-1β fail to bind at all. The selectivity of CC CKR3 mirrors most of the binding activity of primary eosinophils. In fact, when measured by competition against $^{125}$I-eotaxin, the binding affinities on eosinophils for all of these β-chemokines are indistinguishable from those obtained with cloned CC CKR3. Moreover, CC CKR3 was cloned from eosinophils, and as shown by Western blotting is heavily expressed in these cells. The abilities of the different chemokines to activate CC CKR3 are consistent with the binding data as eotaxin, RANTES, and to a lessor extent MCP-3 all stimulate $Ca^{2+}$ fluxes in clones which express the receptor, while MCP-1, MIP-1α and MIP-1β do not, even at concentrations as high as 1 μM. Thus, based on its properties, and expression, CC CKR3, is the eosinophil eotaxin receptor.

TABLE 1

Binding affinities of various chemokines comparing CC CKR3 expressed in AML14.3D10 with primary eosinophils

| | Kd (nM) | |
|---|---|---|
| competitor | CC CKR3 | eosinophils |
| $^{125}$I-human eotaxin | | |
| human-eotaxin | 0.1 ± 0.04 (4) | 0.1 ± 0.03 (3) |
| murine-eotaxin | 0.1 ± 0.04 (3) | 0.1 ± 0.01 (2) |
| MCP-3 | 2.7 ± 1.7 (5) | 3.0 ± 0.2 (2) |
| RANTES | 3.1 ± 0.6 (5) | 2.6 ± 0.3 (2) |
| MCP-1 | 60 ± 9 (3) | 41 ± 2 (2) |
| MIP-1a | N.B. (4) | N.B. (2) |
| MIP-1β | N.B. (4) | N.B. (2) |
| $^{125}$I-MCP-3 | | |
| human-eotaxin | 0.2 ± 0.1 (4) | 0.2 ± 0.1 (2) |
| murine-eotaxin | 0.3 ± 0.1 (2) | 0.2 ± 0.1 (3) |
| MCP-3 | 0.7 ± 0.4 (4) | 1.1 ± 0.6 (10) |

TABLE 1-continued

Binding affinities of various chemokines comparing CC CKR3 expressed in AML14.3D10 with primary eosinophils

| competitor | Kd (nM) | |
| --- | --- | --- |
| | CC CKR3 | eosinophils |
| RANTES | 0.5 ± 0.3 (4) | 0.9 ± 0.4 (8) |
| MCP-1 | 16 ± 2 (3) | 61 ± 13 (2) |
| MIP-1a | N.B. (4) | see text |
| MIP-1β | N.B. (4) | N.B. (2) |

Competition binding experiments were carried out against the indicated iodinated ligand as follows and as described herein. Equilibrium binding of β-chemokines to AML14.3D10 cells expressing CC CKR3 and to primary eosinophils was examined with increasing concentrations of unlabelled human eotaxin, murine eotaxin, RANTES, MCP-3, or MCP-1 to compete against fixed concentrations of either $^{125}$I-human eotaxin, or $^{125}$I-MCP-3. Also the competition with 100 nM concentrations of MIP-1α, and MIP-1β was examined. The experiments were carried out either with AML14.3D10 cells expressing CC CKR3, or with eosinophils. All values are the averages of triplicate determinations. Typically, 4000–6000 cpm of iodinated ligand was bound in the absence of compeititor with SIN ratios exceeding 15. Human and murine eotaxin are the human and murine chemokines, respectively. "N.B." means that no competition was observed. All results are the averages of the number of experiments shown in parenthesis.

Various changes and modifications may be made in the products and processes of the present invention without departing from the spirit and scope thereof. The various embodiments and the examples which have been set forth herein are given for the purpose of illustrating the present invention and shall not be construed as being limitations on the scope or spirit of the instant invention.

EXAMPLE 1
mRNA Isolation and cDNA Cloning

Total RNA was isolated from purified eosinophils with TRIzol reagent (BRL) and used in a RT/PCR reaction (Daugherty, B. L., et al. (1991) Nucleic Acids Research 19, 2471–2476) using oligonucleotide primers designed from the human CC CKR1 and MCP-1RB cDNA sequences (Neote, K., et al. (1993) Cell 72, 415–425; Charo, I. F., et al. (1994) Proceeding of the National Academy of Sciences 91, 2752–2756). The primers used for PCR corresponded to a consensus sequence encoded in transmembrane domains (TM) II and VII:

5'-PCR primer (TMII) (SEQ ID NO:5):
   5'-AACCTGGCCAT(C,T)TCTGA(C,T)CTGC-3'
3'-RTIPCR primer (TMVII) (SEQ ID NO:6):
   5'-GAAC(C,T)TCTC(C,A)CCAACGAAGGC.

The resultant PCR product of ~700 bp was subcloned into plasmid pNoTA (Five Prime, Three Prime, Inc) and sequenced using Sequenase (USB). The remaining 5' and 3' sequence encoding CC CKR3 was cloned by rapid amplification of cDNA ends (RACE) using both the 5'-RACE and 3'-RACE kits (Clontech) with the following primer sequences:
(5'-RACE) (SEQ ID NO:7):
   5'-TCTCGCTGTACAAGCCTGTGTG-3';
(3'-RACE) (SEQ ID NO:8):
   5'-CCTTCTCTCTTCCTATCAATCC-3'.

The resultant PCR products (5'-RACE, ~450 bp; 3'-RACE, ~700 bp) were subcloned into pCRII (Invitrogen) and sequenced. Upon identification of the 5'-end of the cDNA containing the initiator ATG codon and the 3'-end containing the termination codon TAG, a new set of PCR primers were designed to reamplify the entire coding region from eosinophil total RNA for expression of CC CKR3. The primer sequences used for RT/PCR were:

5'-PCR primer (SEQ ID NO:9):
   5'-ATATATTAAGCTTCCACCATGACAACCTCACTAG-ATACAG-3';
3'-RT/PCR primer (SEQ ID NO: 10):
   5'-ATATATTCTAGAGCGGCCGCTAAAACACAATAG-AGAGTTCC-3'.

The resultant PCR product of 1105 bp was digested with HindIII and NotI and subcloned into plasmid pBJ/NEO to yield pBJ/NEO/CCCKR3. The plasmid pBJ/NEO was prepared essentially as follows. Plasmid pD5/Igh/Neo (Daugherty, B. L., et al. (1991) Nucleic Acids Research 19, 2471–2476) was digested with the restriction enzyme SalI, filled in with E. coli DNA polymerase I Klenow fragment to create a blunt end and subsequently digested with the restriction enzyme NotI. The CMVIE intron A fragment from plasmid p89-11 was digested with ClaI, filled in to create a blunt end and subsequently digested with HindIII. These fragments were used in a three-way ligation with a HindIII and NotI fragment of the human C5a receptor cDNA. The C5a receptor fragment was excised with HindIII and NotI and replaced with the eotaxin receptor cDNA of 1105 bp obtained by RT/PCR with oligonucleotides SEQ ID NO:9 and SEQ ID NO: 10 after digestion with HindIII and NotI. Several clones were sequenced and one clone comprising the consensus sequence was chosen for expression of CC CKR3 in heterologous cells.

EXAMPLE 2
Transfection into AML14.3D10 Human Eosinophilic Cell Line

AML14.3D10 cells (Paul, C. C., et al. (1995) Blood 86, 3737–3744) were cultured in RPMI-1640, 10% FBS, 1 mM sodium pyruvate, 0.5 µM β-mercaptoethanol and 2 mM L-glutamine (complete medium). Cells were harvested at a density of 0.3×10$^6$/mL, washed once in PBS, resuspended in RPMI at 10$^7$/mL, and 25 µg of plasmid was added. Electroporation was carried out at 300 V, 960 µF using a Gene Pulser (BioRad). Following electroporation, cells were chilled at 0° C. for 10 min and then plated in complete medium at 10$^6$/T75 flask and cultured at 37° C., 5% CO$_2$. After 16–24 hr, cells were pelleted and resuspended in complete medium containing 2 mg/mL Geneticin (GIBCO). Cells were maintained in selection medium for 8–10 days until individual surviving clusters appeared. Invididual cells were then transferred to 96-well plates and expanded. AML14/CCCKR3 sublines were assayed for the ability to generate a Ca$^{2+}$ flux in response to either RANTES or eotaxin. Positive sublines were then probed by western blotting with an antibody raised against the predicted C-terminus of CC CKR3. Cell lines positive in both sets of assays were then characterized for their ability to bind to a variety of CC chemokines, including eotaxin, RANTES, MCP-3, MIP-1α, MIP-1β, and MIP-1.

EXAMPLE 3
Purification of Eosinophils

Primary eosinophils were isolated from granulophoresis preparations obtained from allergic and asthmatic donors (Bach, M. K., et al. (1990) Journal of Immunological Methods 130, 277–281). The leukocytes were mixed with equal volumes of HBSS and layered over LSM (Organon Teknika) as described (Rollins, T. E., et al. (1988) *Journal of Biological Chemistry* 263, 520–526). After lysis of erythrocytes with NH$_4$Cl, the granulocytes were subsequently treated with anti-CD16 microbeads followed by MACS separation (Miltenyl Biotech) (Hansel, T. T., et al. (1991) *Journal of Immunological Methods* 145, 105–110). Typically the eosinophil preparations were >99% pure as determined using the LeukoStat staining kit (Fisher).

EXAMPLE 4
Generation of α-CC CKR3 Antisera and Immunoblotting

Polyclonal rabbit antisera was generated to CC CKR3 using the C-terminal decapeptide sequence TAEPELSIVF. Peptide synthesis, coupling to thyroglobulin and production of antisera was performed (Miller, D. K., et al. (1993) *Journal of Biological Chemistry* 268, 18062–18069). Whole cells were boiled and sonicated in Laemli sample buffer (Laemmli, U. K. (1970) *Nature* 227, 680–685), electrophoresed on 4–20% SDS gels (Novex), transferred to polyvinylidene difluoride membranes (BioRad), and blocked with 5% nonfat dry milk in TBST (20 mM Tris, 200 mM NaCl, 0.1% Tween-20) for 16 hr at 4° C. The membrane was incubated with antisera at 1:1000 in TBST for 1 hr at room temperature, washed, and subsequently incubated with goat anti-rabbit HRP (Zymed) at 1:4000 in TBST for 30 min also at room temperature. After washing, the membrane was treated with ECL western blotting reagents (Amersham) for 1 min, covered in plastic wrap and exposed to film for 2 min.

EXAMPLE 5
Chemokine Binding Assays

Recombinant MCP-3, MCP-1, RANTES, murine and human eotaxin were obtained from Peprotech (Princeton, NJ). $^{125}$I-MCP-3 and $^{125}$I-MIP-1α were obtained from New England Nuclear (Boston, Mass.), and $^{125}$I-human-eotaxin was obtained from Amersham. Binding of $^{125}$I-labeled ligands (typically a total of 2×10$^4$ cpm) in the presence of varying concentrations of unlabeled ligands to intact cells (typically 1.5×10$^4$, 10$^5$, or 10$^6$ for experiments with labeled eotaxin, MCP-3, or MIP-1α, respectively) were performed at 32° C. (Van Riper, G., et al. (1993) *Journal of Experimantal Medicine* 177, 851–856).

EXAMPLE 6
Ligand-induced Ca$^{2+}$ Fluxes

Human CC CKR3 expressing AML14 clones or purified eosinophils were incubated with 1.25 μg/ml Indo-I (Molecular Probes, Eugene, Oreg.) in RPMI 1640, 10 mM HEPES, 5% FBS, for 60 min at 37° C. (Van Riper, G., et al. (1993) *Journal of Experimantal Medicine* 177, 851–856). Loaded cells were washed and incubated at 37° C. before the addition of ligands. Calcium fluxes were performed on a FACS analyzer (Becton Dickinson & Co., Mountain View, Calif.) with an excitation wavelenth of 365 nm and dual emission wavelength of 405 and 488 nm.

EXAMPLE 7
CC CKR3 Binding Assay

Assay buffer (50 mM Hepes, pH 7.2 w/0.5% BSA, 5 mM MgCl$_2$, 1 mM CaCl$_2$, 100 uM PMSF and 10 ug/ml phosphoramidon, leupeptin, aprotinin and chymostatin), test compound (or equivalent volume of solvent), 20 pM $^{125}$I-human eotaxin (2000 Ci/mmol), 25 ng unlabeled human eotaxin (non-specific binding wells only), and AML14.3D10 cells expressing eotaxin receptor cells, or eosinophils, are added sequentially in 96-well, round-bottom, polystyrene plates to a final volume of 250 uL. Assay plates are then mixed and incubated for 60 minutes at 31° C. After incubation, assay plates are harvested onto Packard 96-well GF/C Unifilter plates treated with 0.33% polyethylenimine (PEI) using Packard Filtermate 196 cell harvester. Wells and filters are washed with 200 uL 50 mM Hepes, pH 7.2 with 0.5M NaCl and 0.02% NaN$_3$. After filtration, GF/C plates are dried and sealed. 25 uL Packard Microscint-O scintillant are then added to each well and counted for 2 minutes on Packard Topcount (liquid $^{125}$ setting).

EXAMPLE 8
Phosphoinositide 3-kinase (PI-3K) Assay

AML14.3D10 expressing eotaxin receptor (CCCKR3) cells are incubated with test compound and stimulated with eotaxin, RANTES, or MCP-3, pelleted and lysed in 1 mL lysis buffer (1% Nonidet P-40, 100 mM NaCl, 20 mM Tris, pH 7.4, 10 mM iodoacetamide, 46 mM b-glyceraphosphate, 10 mM NaF, 1 mM PMSF, 1 ug/mL leupeptin, 1 ug/mL chymostatin, 1 ug/mL antipain, 1 ug/mL pepstatin A, and 1 mM sodium orthovanadate). Lysates are then pre-cleared for 1 hr with uncoupled protein A Affi-Gel beads. Immunoprecipitation is then performed with p85 polyclonal antiserum (1 ul/mL lysate; Upstate Biologics, New York, N.Y.), coupled to protein A Affi-Gel beads (Bio-Rad) at 4° C. for 2 hr. Immunoprecipitates are washed and subjected to in vitro lipid kinase assays by using a lipid mixture, 100 ul 0.1 mg/ml PtdIns and 0.1 mg/ml phosphatidylserine dispersed by sonication into solution in 20 mM HEPES, pH 7.0, and 1 mM EDTA. The reaction is initiated by the addition of 100 mM ATP and 20 uCi [gamma-$^{32}$P]ATP (3000 Ci/mmol) in 20 ul kinase buffer. The reaction is then terminated after 15 min and the phosphoinositide lipids are separated by thin layer chromatography (TLC) and visualized by exposure to iodine vapor autoradiography.

EXAMPLE 9
Chemotaxis Assay

AML14.3D10 expressing eotaxin receptor cells are isolated by centrifugation (van Riper, G., et al. (1994) *J. Immunol.* 152, 4055–4061) for 15 min at 150×g, washed and resuspended at 10$^7$ cells/ml in HBSS (pH 7.4) containing 1 mM CaCl$_2$ and 1 mM MgCl$_2$ (chemotaxis buffer). The chemotaxis experiments is then performed in Transwell dishes (6.5 mm, Costar, Cambridge, Mass.). The lower chamber contains 0.6 ml of chemotaxis buffer and is separated from the upper chamber containing 10$^6$ cells by a 5-mm pore Nucleopore polycarbonate membrane (Nucleopore Corporation, Pleasanton, Calif.). After a 15 min preincubation at 37° C., test compound and eotaxin, RANTES, or MCP-3 are added to the lower chamber to a final concentration of 300 nM. After 2 hrs at 37° C., the upper chamber inserts are removed, and the cells that migrate to the lower chamber are enumerated by a Coulter Counter (Coulter Electronics, Hialeah, Fla.).

EXAMPLE 10
Ligand-Dependent Inositol Phosphate Release Assay

AML14.3D10 expressing eotaxin receptor cells are labeled with [$^3$H] inositol (10 uCi/ml) for 24 hrs as described (Wu, D., et al. (1993) *Science* 261, 101–103). Test compound and arious concentrations of eotaxin, MCP-3, or RANTES are then added to the cells for 30 min. The cells are lysed in 10% perchloric acid, neutralized in 2 N KOH and centrifuged. The supernatant is transferred to columns containing 0.5 ml AG1-X8 anion exchange resin, washed with 6 ml borax buffer and eluted with 0.3 ml formic acid (0.1 M). The eluted samples are mixed with scintillation cocktail and counted.

EXAMPLE 11

Acidification Rate Assay

AML14.3D10 expressing eotaxin receptor cells are subject to serum starvation for 16 hrs. The cells are then mixed at a 3:1 (v/v) ratio with low melting temperature agarose. A 10 ul drop of the cell/agarose mixture is pipetted into a sterile Capsule Cup (Molecular Devices) at a cell density of approximately 200,000 cells/cup. The cell/agarose drop forms a gel after about 5 min, and is assembled into the cup between two 3 um porosity polycarbonate membranes with running medium. The assembled capsule cups is placed into the sensor chambers and then placed on the Cytosensor Microphysiometer (Molecular Devices) containing 1 ml of running medium. The chambers are allowed to equilibrate for 1 hr at 37° C. with a flow rate of 100 ul/min. The experiment is initiated with an 8 min exposure of eotaxin, RANTES, MCP-3 and test compound at various concentrations and the acidification rate over baseline will be measured in the medium (McConnell, H. M., et al. (1992) *Science* 257, 1906–1912) until the cells return to the unstimulated level.

EXAMPLE 12

Actin Polymerization Assay

AML14.3D10 expressing eotaxin receptor cells are diluted in APA buffer (HBSS; 25mM Hepes; 0.2% BSA, pH7.2) at a concentration of $4 \times 10^6$/ml. One ul of test compound and eotaxin, RANTES, or MCP-3 added into a 96-well plate and incubated at 37° C. 100 ml of cells are added to the plate and incubated for 20 sec to which 100 ml of APA cocktail (2 mls 8% formaldehyde; 460 uLs 0.33 uM Rhodamine-phalloidin; 1.85 mg 200 ug/ml lysolecithin; 7.25 mls HBSS) is added. Plates are then centrifuged at 2000 RPM for 5 min, cleared and then 100 ul of HBSS is added to all wells which are read in a Fluoroskan II fluorometer.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, procedures other than the particular experimental procedures as set forth herein above may be applicable as a consequence of degeneracy and variations in the sequences of the proteins and DNA of the invention indicated above. Likewise, the characterization data observed may vary slightly according to and depending upon the particular assay or characterization method employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A recombinant human eosinophil eotaxin receptor having the amino acid sequence as set forth in SEQ ID NO:1.

2. The receptor of claim 1 wherein the receptor is expressed by a host cell which does not naturally express the human eosinophil eotaxin receptor.

3. The receptor of claim 1 wherein the receptor is expressed by a host cell which is from the AML14.3D10 cell line.

4. The receptor of claim 1 which binds each of eotaxin, RANTES and MCP-3.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 355 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

```
Met Thr Thr Ser Leu Asp Thr Val Glu Thr Phe Gly Thr Thr Ser Tyr
 1               5                  10                  15

Tyr Asp Asp Val Gly Leu Leu Cys Glu Lys Ala Asp Thr Arg Ala Leu
            20                  25                  30

Met Ala Gln Phe Val Pro Pro Leu Tyr Ser Leu Val Phe Thr Val Gly
        35                  40                  45

Leu Leu Gly Asn Val Val Val Met Ile Leu Ile Lys Tyr Arg Arg
    50                  55                  60

Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
                85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
        115                 120                 125
```

```
Ile Asp Arg Tyr Leu Ala Ile Val His Ala Val Phe Ala Leu Arg Ala
    130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Leu
        195                 200                 205

Val Leu Pro Leu Leu Val Met Ala Ile Cys Tyr Thr Gly Ile Ile Lys
    210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
            260                 265                 270

Cys Glu Arg Ser Lys His Leu Asp Leu Val Met Leu Val Thr Glu Val
        275                 280                 285

Ile Ala Tyr Ser His Cys Cys Met Asn Pro Val Ile Tyr Ala Phe Val
    290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355

(2) INFORMATION FOR SEQ ID NO:2:

(i) SEQUENCE CHARACTERISTICS:
        (A) LENGTH: 1065 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

ATGACAACCT CACTAGATAC AGTTGAGACC TTTGGTACCA CATCCTACTA TGATGACGTG      60

GGCCTGCTCT GTGAAAAAGC TGATACCAGA GCACTGATGG CCCAGTTTGT GCCCCCGCTG     120

TACTCCCTGG TGTTCACTGT GGGCCTCTTG GGCAATGTGG TGGTGGTGAT GATCCTCATA     180

AAATACAGGA GGCTCCGAAT TATGACCAAC ATCTACCTGC TCAACCTGGC CATTTCGGAC     240

CTGCTCTTCC TCGTCACCCT TCCATTCTGG ATCCACTATG TCAGGGGCA TAACTGGGTT      300

TTTGGCCATG GCATGTGTAA GCTCCTCTCA GGGTTTTATC ACACAGGCTT GTACAGCGAG     360

ATCTTTTTCA TAATCCTGCT GACAATCGAC AGGTACCTGG CCATTGTCCA TGCTGTGTTT     420

GCCCTTCGAG CCCGGACTGT CACTTTTGGT GTCATCACCA GCATCGTCAC CTGGGGCCTG     480

GCAGTGCTAG CAGCTCTTCC TGAATTTATC TTCTATGAGA CTGAAGAGTT GTTTGAAGAG     540

ACTCTTTGCA GTGCTCTTTA CCCAGAGGAT ACAGTATATA GCTGGAGGCA TTTCCACACT     600

CTGAGAATGA CCATCTTCTG TCTCGTTCTC CCTCTGCTCG TTATGGCCAT CTGCTACACA     660
```

```
GGAATCATCA AAACGCTGCT GAGGTGCCCC AGTAAAAAAA AGTACAAGGC CATCCGGCTC      720

ATTTTTGTCA TCATGGCGGT GTTTTTCATT TTCTGGACAC CCTACAATGT GGCTATCCTT      780

CTCTCTTCCT ATCAATCCAT CTTATTTGGA AATGACTGTG AGCGGAGCAA GCATCTGGAC      840

CTGGTCATGC TGGTGACAGA GGTGATCGCC TACTCCCACT GCTGCATGAA CCCGGTGATC      900

TACGCCTTTG TTGGAGAGAG GTTCCGGAAG TACCTGCGCC ACTTCTTCCA CAGGCACTTG      960

CTCATGCACC TGGGCAGATA CATCCCATTC CTTCCTAGTG AGAAGCTGGA AAGAACCAGC     1020

TCTGTCTCTC CATCCACAGC AGAGCCGGAA CTCTCTATTG TGTTT                    1065

(2) INFORMATION FOR SEQ ID NO:3:

(i) SEQUENCE CHARACTERISTICS:
        (A) LENGTH: 3586 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGATCCCTAC CTTCCCCATC AGAGCTAGGG GGCATGGAGC GCTCTCTGCT AAGATGGGGA       60

CCCCCAAGGA ATGTCTCCCT GTGGGGCACT TCCTTACCAG ATGGGATGGC CAGTGCGGTT      120

AAGTTGGTGG TCAGGCAGAA AAAAAGATC TAGTTTGTAC TCTTGAGAGT TCCTCGGTTT       180

GTTCATGGCA TGGGCAGGGA GTCAAGGAGC AGCAGCCTTG CCTCAGTGCC TACCAGTGCA      240

GGAAAAGGTG CATAGCCTGG GCCAGGGCCA GGGCCCTGGT GGAGGCGTAG TGGTAACAGA      300

GAGGGCTCTC CATTCCAGCC CAAGGAAGAC TAAGAATGAA TACCTCATGA GTATATTAGC      360

TACAAACCAC CACAGCAGGT TCCAGAAAAA GGCTCAGCGT TGGAACCAGG TCACCCCCAC      420

TCAGCAGACA CCAGTCATAT AAATCAAGGA CCAACAGGAG ACAGGAACAC CCCCTTCCCA      480

CTCTGCCCCA TGTCTCAAGT TGTAGTGGCC CTTCCTCCAG ATCTCTGCCA CCATCTTAGA      540

AAGGAACACT GAAAGAAGAA ACTGAAATTA TAAGCTGACA GCATAAAGAG GATGAGTAAA      600

ACCTAAAATC ATTGTTCACA TGAATGAATC AAGAGAAGTT TAAACCACTT TGGACTAAAA      660

TGTGTGAATC CTTTTTCCTG CTATCCAGCA GATGAGAAGC TGGTAACAGA GACCACAATA      720

GTTTGGAGAC TAAAGAATCA TTGCACATTT CACTGCTGAG TTGTATTGTG AGTAATTTTA      780

GTTGACCTCA CTTTGTAAAT CTTGCACACG GGGCAATCCA ATATCTGCAC AAGAGATATG      840

TTAACCAGTG GTAAATGCTG CATGAGGAGA TTGGGTGATT TTTACTTTCG TTTTTGTGCT      900

CTTCTTTCTT ATTGTTCTTA CTTATTTACG ATTACCCTAT CGTTTTCCCA AAATGTAAAA      960

GGCCATTTTG AAAGCCTAAT TCAAACCTCT TCACTATTTT GTATCTAAGT ATTCACCTTG     1020

ATTGAGACTG GGTAGACAGG TGAAAACCAT ATCAGGTTTT TAATTTTTTA ATTTTTAATT     1080

ATTTATTTAT TTATTTATTT TTTGAGATGG AGTCTGGCTG TCGCCCAGGC TGGAGTGCAG     1140

CGGCGTGATC ACAGTTCACT GCAGCCTCAA CCTTCTAGGC TCAAGGGATT CTCCCACCTC     1200

AGCCCCCCAA GTAGTTGGGA CCACACGTAT GCGCACCAT GCCTGGCTAA TTTCTTATTT      1260

TTTTGTAGAG ATAGGATCTC ACTATATTGT CCAGGCTGGT CTTGAATTCC TGGGCTCAGG     1320

TGAGCCTCCC ACCTGGGCCT CCCAAAGTAC TGGGATTACA GGCATGAGCC AAGGTCCCCT     1380

GCCCATATGA GATTTTCTGT CTCTGATCCC ATGCAGCTAG TAATCAAGGA CTTGGCTGCT     1440

GACTCTGGAG GACCTGCATG CTTTCTTGAG CTGTGAACTT CAGTGCTAAA AGCTCATAGG     1500

CAGCCCTGAA ACCCAAACCA AAAGGTTCTA TGGTTTATCA TCCTGATCAT GTTGATTTTA     1560
```

```
TAGAAATAAC ACATGAATTA AAGACACTAC CCTCAAACTG AGCAAAACTT AAGTAATTTT    1620

TTTAAAGTTT GACCTGTTTT TAAATCACTC TTGGAGAAAA AGGAAAATAA ATACAAATAA    1680

TTAACGGTGA ATACAGGCTA CTATACCTTT GTTCTCCAGA ATTAGCAGTT CTGTTCTTTT    1740

CTTGCTTTAG ATGCTGAAGT GCAGAAGGAC ACTCTGTGAT TGTACGTGTG TAACTGACAA    1800

AATGTGTATT TTTTTTCTCA GCTGCTATGG ATTGGATTAT GCTATTATGA ATAAGAATGC    1860

TGATGGGAGC ACACACAAAC CATTTGTTCC TCAGTCCATT TTCCTCCTCA AAAGCCTGGA    1920

ATGTGCCATT GATCAGTGGG AGATGTACCT GGACAGACCC ATGAAAAGAG ATCAACAAGT    1980

TCCACCCAAG GGACCCTATT TTTCCTAATT TCATTTGAAA TGGCTTCTAA TTGTCCTTCT    2040

TTCATTCCTG CTTCCTACCA GTTTTACAGC TTTTTCTGGT TTCAAATGTG AACTCACATA    2100

CACTCTCATT TTTCCTCATC ACAACCCCAA GTGACCCAAT GGTCCTCACT TTCGATATAA    2160

GTAAAGGAGG CTCTGCATTA AGGGCTTGTC CAAGGCACGC AGCTGAGAGG CGCTAGGACT    2220

GGCTCCATTT CCATCTCTAT TCTCACTGAC TTTGACTACC CAGAACCCCA ACATGTGGGG    2280

CCTCAGTATT CGATCAATTA TTCTATTAAG AAGCAAAAAC AATTCCCCGC ATTGGCCCCA    2340

GTTATTAAGC ATTTCTCAGA TTTACCTTGA GAAATGCCCA TCGGCCTGTA TATTCACATC    2400

TTCACCCTTG TCCCTTCCTC CTAGAAAGGA GAAAGTCAGT TGGATGCCCT CTGAGGAACT    2460

AGTGCATGGC TTAACTGTCC TTCCATGACT CCTGCCTTAT CTGTTTTCTA TTTTCCTCCT    2520

TTTCCACCGA AGTCTATAAT CTCAAGAAAA GCAGGCACTG GCCTTAGGGC TCCTGGCCTA    2580

AGAAATATCA AGTCCAGTGA GAAATCCCAT TGACTGACCC CTCCTGCTTA CCCCTTTGTG    2640

ATGGAGAAGC TCCCAGGGGT TTGCTTTTTG CATGTTACCA GGCCTAACTC AGCATCACCA    2700

GGGGCAAGAA AAGGAAAGTA ACCTAAACTA ATGCTGCTTA TAATTGTAAT TATTGTAATA    2760

GTTAATTACT GTGATTGTAC ATGTGTAACA GACAAAATGT GTATTTTTTT CACAGCTGCT    2820

GTGGATTGGA TTATGCCATT TGGAATAAGA ATGCTGTTAA GAGCACACAA GCCAGGTTCC    2880

TCAAGTCCGT AGCAAATTTT TCAAAAGTTA AATTTAAAAA TCACTACATT TGAATCTAGT    2940

GACAGGAGAA ATGGACATGG ATAGAGACTA AAGATCTAGC CCAAATTTTA TATTTACTTG    3000

TTAGAGGATT TTGAACAAAT TACTAAATTT CTTCAAGGTT CAATTTCCCC ATTAACTATA    3060

ATGAATGTCT CATCATTATG GGGCCCTGGA GAAGCATAAT TACTTGTAAT TGTAATAATC    3120

ATTGTTATTA TTATTATACA TATTTTGCTT TTAAATGGAT AAGGATTTTT AAGGTATATG    3180

TAAACTGTAA AACATAAAAT GCAAAATGCC GTAAGAGACA GTAGTAATAA TAATGATTAT    3240

TATATTGTTA TCATTATCTA GCCTGTTTTT TCCTGTTGTG TATTTCTTCC TTTAAATGCT    3300

TACAGAAATC TGTATCCCCA TTCTTCACCA CCACCCCACA ACATTTCTGC TTCTTTTCCC    3360

ATGCCGGTCA TGCTAACTTT GAAAGCTTCA GCTCTTTCCT TCCTCAATCC TTCTCCTGGC    3420

ACCTCTGATA TGCCTTTTGA AATTCATGTT AAAGAATCCC TAGGCTGCTA TCACATGTGG    3480

CATCTTTGTT GAGTACATGA ATAAATCAAC TGGTGTGTTT TACGAAGGAT GATTATGCTT    3540

CATTGTGGGA TTGTATTTTT CTTCTTCTAT CACAGGGAGA AGTGAA              3586

(2) INFORMATION FOR SEQ ID NO:4:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: cDNA
```

-continued (xi) SEQUENCE DESCRIPTION: SEQ ID NO:4:

```
TAGGTCAGAT GCAGAAAATT GCCTAAAGAG GAAGGACCAA GGAGATGAAG CAAACACATT      60

AAGCCTTCCA CACTCACCTC TAAAACAGTC CTTCAAACTT CCAGTGCAAC ACTGAAGCTC     120

TTGAAGACAC TGAAATATAC ACACAGCAGT AGCAGTAGAT GCATGTACCC TAAGGTCATT     180

ACCACAGGCC AGGGGCTGGG CAGCGTACTC ATCATCAACC CTAAAAAGCA GAGCTTTGCT     240

TCTCTCTCTA AAATGAGTTA CCTACATTTT AATGCACCTG AATGTTAGAT AGTTACTATA     300

TGCCGCTACA AAAAGGTAAA ACTTTTTATA TTTTATACAT TAACTTCAGC CAGCTATTGA     360

TATAAATAAA ACATTTTCAC ACAATACAAT AAGTTAACTA TTTTATTTTC TAATGTGCCT     420

AGTTCTTTCC CTGCTTAATG AAAAGCTT                                        448
```